United States Patent [19]

Szabó et al.

[11] Patent Number: 4,820,852

[45] Date of Patent: Apr. 11, 1989

[54] PROCESS FOR THE PREPARATION OF DIACYL-DIANHYDRO HEXITOLS

[75] Inventors: Tibor Szabó; Ildikó Vidra née Sándor; Gyula Dalmadi; Judit Kaczmarek née Sebestyén; János Őri, all of Budapest, Hungary

[73] Assignee: Chinoin Gyogyszer es Vegyeszeti Termekek Gyara, Budapest, Hungary

[21] Appl. No.: 178,876

[22] PCT Filed: Jan. 16, 1985

[86] PCT No.: PCT/HU85/00002

§ 371 Date: Nov. 4, 1985

§ 102(e) Date: Nov. 4, 1985

[87] PCT Pub. No.: WO85/03293

PCT Pub. Date: Aug. 1, 1985

Related U.S. Application Data

[63] Continuation of Ser. No. 778,186, Nov. 4, 1985, abandoned.

[30] Foreign Application Priority Data

Jan. 18, 1984 [HU] Hungary .................... 194/84

[51] Int. Cl.[4] .................................. C07D 301/00
[52] U.S. Cl. .................... 549/539; 549/557
[58] Field of Search .......................... 549/539, 557

[56] References Cited

U.S. PATENT DOCUMENTS 4,100,173 7/1978 Gerecke et al. .................. 549/354
4,419,522 12/1983 Elekes et al. .................... 549/557

FOREIGN PATENT DOCUMENTS 51467 5/1982 European Pat. Off. ..
2557033 7/1976 Fed. Rep. of Germany .
1490649 11/1977 United Kingdom .

OTHER PUBLICATIONS

W. Steglich et al., Angew. Chemie, Internat. Edit., vol. 8(12) (1969) p. 981.
G. Höfle et al., Synthesis, Nov. 1972, pp. 619–621.
W. Steglich et al., Tetrahedron Letters, No. 54, (1970), pp. 4727–4730.
A. Hassner et al., Tetrahedron Letters, vol. 34, (1978) pp. 2069–2076.
M. Jarman, Carbohydrate Research, 9, pp. 139–147 (1969).

*Primary Examiner*—Richard L. Raymond
*Attorney, Agent, or Firm*—Herbert Dubno; Jonathan Myers

[57] ABSTRACT

The subject of the invention is an improved process for the industrial scale preparation of the compounds of the formula

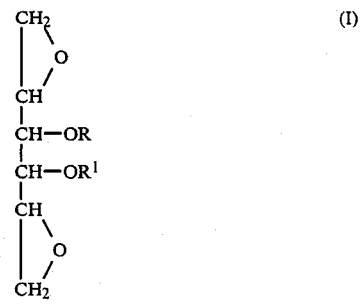

and salts thereof by acylating the hexitols of the formula (II) with an anhydride of the formula (II) at a temperature of 0°–30° C. in the presence of an organic base and a catalyst of the formula (IV) in a dipolar-aprotic or aprotic solvent.

5 Claims, No Drawings

PROCESS FOR THE PREPARATION OF DIACYL-DIANHYDRO HEXITOLS

This is a continuation of co-pending application Ser. No. 778,186 filed on Nov. 4, 1985, now abandoned.

FIELD OF INVENTION

The present invention relates to an improved process for the preparation of the diacyl-dianhydro hexitols of the formula (I) and salts thereof exhibiting cytostatic effect. By the aid of the process of the invention the compounds of the formula (I) can also be prepared on an industrial scale.

In the formula I

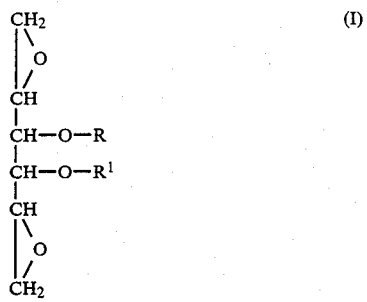

R and $R^1$ are independently an alkanoyl group having 1 to 6 carbon atoms optionally substituted by a free carboxyl group, alkoxycarbonyl having 2 to 5 carbon atoms or chlorine; aroyl having 7 to 11 carbon atoms, cycloalkylcarbonyl having 7 to 11 carbon atoms, 2-furanoyl or alkylarylcarbonyl having 8 to 11 carbon atoms.

and the configuration of the hexitol skeleton is that of dulcitol, mannitol or iditol.

Throughout this specification, unless otherwise stated, the meaning of the substituents is the same as defined hereinabove.

BACKGROUND ART

It is known in the art that the compounds of the formula (I) can be prepared by acylating the compounds of the formula

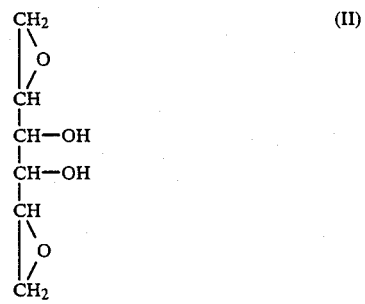

(DOS No. 2,557,033, European Patent Application No. 51,467). This reaction cannot be considered as a simple acylation. The starting materials as well as the target products can suffer decomposition and the rate of these undesired side-reactions highly depends on the quality and the quantity of the other substances being present in the mixture. E.g. in the presence of acids and bases the compounds undergo trans-cyclization, a 3,6-anhydro ring is formed, the ring can open up, polymerization occurs, etc. The presence of electrolytes, e.g. salts of halogenic acids leads to the formation of the corresponding halogen derivatives. The rate of the decomposition sharply increases with any increase to the temperature.

Due to the undesirable side-reactions a significant portion of the starting materials is transformed into by-products and the amount of the target compound to be prepared is further diminished by the decomposition reactions, therefore the yield of the reaction is highly decreased.

A further problem arises when compounds containing free carboxyl groups are to be prepared by using an acid anhydride as acylating agent. The salt of the monoacyl derivative of the hexitol formed in the first step with the acid binding agent separates from the reaction mixture due to the use of an unsuitable solvent and the diacyl derivative is formed only with poor yields.

When the known processes were attempted on a large scale it was found that they can be reproduced with the reported yields only a laboratory scale (10 millimoles). Using the starting material in an amount of 1,46 kg (10 moles) the 1,2-5,6-dianhydro-3,4-bis($\beta$-carboxypropionyl)-dulcitol could be prepared only with a yield of 4 to 40% instead of 8 to 88%. A further disadvantage of the process is that as $\beta$-carbobenzyloxy propionyl chloride is highly susceptible to decomposition, this compound has to be prepared just before the acylation from succinic acid anhydride through succinic acid monobenzylester and this fact further decreases the usability of the process on a large scale.

The object of this invention is to work out a process enabling the industrial scale preparation of the compounds of the formula (I) without using agressive reagents, within short reaction and operation times and at lower temperatures in a reaction medium wherein the monoacyl intermediates comprising free carboxyl groups and the salts of the obtained products with organic bases can be well dissolved.

SUMMARY OF THE INVENTION

Surprisingly we found that the compounds of the formula (I) can be prepared by reacting the hexitols of the formula (II) with an anhydride of the formula (III)

wherein
A and B independently stand for alkyl having 1 to 5 carbon atoms optionally substituted by chlorine or alkoxycarbonyl having 2 to 5 carbon atoms, phenyl, cycloalkyl having 6 to 10 carbon atoms, alkylaryl having 8 to 10 carbon atoms, 2-furyl, or together form an aryl of 6 to 10 carbon atoms or an alkylene group having 2 to 5 carbon atoms,
in the presence of a catalyst of the formula (IV)

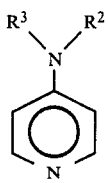

wherein

R² and R³ independently stand for alkyl having 1 to 6 carbon atoms or together form an alkylene group having 1 to 6 carbon atoms optionally substituted with one or two dimethyl-amino groups, and an organic base in a dipolar-aprotic or aprotic solvent.

The compounds of the formula (I) obtained are preferably recovered by evaporating and crystallizing the reaction mixture or decomposing the reaction mixture and extracting it with an organic solvent, thereafter evaporating and crystallizing the extract thus obtained, and the end-product is optionally purified in a manner known per se, preferably by a chromatographic method.

DETAILED DESCRIPTION OF THE INVENTION

According to a preferred embodiment of the process of the invention the acylation is carried out between 5 and 25° C. and a trialkyl amine, preferably triethyl amine is used as an organic base. Preferably dimethyl sulfoxide, dimethyl formamide, sulpholane or diethyl formamide is employed as a dipolar-aprotic solvent, while benzene, carbon tetrachloride or chloroform is used as an aprotic solvent.

The catalysts of the formula (IV) are preferably used in an amount of 0.01 to 2 moles calculated per mole of starting material of the Formula (II). In this case the reaction runs within 30 minutes.

In the above dipolar-aprotic solvents the salts of the endproducts comprising free carboxyl groups and the intermediates formed with organic bases, e.g. trialkyl amines can well be dissolved therefore they remain in the liquid phase in the course of the reaction.

Both the compounds of the formula (II) and the catalysts of the formula (IV) are known in the art (Carbohydrate Research 9, 139, (1969), Chem. Ind. 42., 1789, (1967), (Angew. Chemie Internat. Ed. 8., 981 (1969), Tetrahedron Letters 4727 (1970), Synthesis 619 (1972), Tetrahedron 34, 2069 (1978)). The compounds of the formula (III) are commercial products and they have been known in the art for a long time.

The process of the invention is illustrated by the following, non-limiting examples.

EXAMPLE 1

1,2-5,6-dianhydro-3,4-diacetyl dulcitol 1.35 kg of 1,2-5,6-dianhydro-dulcitol are suspended in 22.4 l of dry benzene then 2.94 l of triethyl amine and 2.0 l of acetic acid anhydride are added under stirring, thereafter the reaction mixture is cooled to 10° C. 12 g (10.1 millimoles) of 4-dimethylamino pyridine are charged to the reaction mixture at a temperature of 10° C. under stirring, and the solution is stirred for 15 minutes after the cooling is ceased. Thereafter 12 l of 10% sodium chloride solution are added and the mixture is stirred for 10 minutes and the organic phase is separated. 6 l of benzene are charged to the aqueous phase and the benzene solutions are combined and dried over 1 to 2 kg of anhydrous sodium sulphate. After filtering the solution, a portion of the benzene is evaporated under reduced pressure by the aid of a bath having a lower temperature than 40° C., and the residue comprising about 5 l of benzene is crystallized from 23 l of petrolether. Yield: 2,12 kg (92%) of 1,2-5,6-dianhydro-3,4-diacetyl-dulcitol. Melting point: 92°–93° C.

EXAMPLE 2

1,2-5,6-dianhydro-3,4-bis(β-carboxypropionyl)-dulcitol 1.46 g of 1,2-5,6-dianhydro-dulcitol, 2.2 kg of succinic acid anhydride and 3.04 l of triethyl amine are dissolved in 3.0 l of dimethyl sulphoxide and the solution is cooled to 5°–10° C. Thereafter 122 g (1 mole) of 4-dimethylamino pyridine are added to the reaction mixture under stirring at a temperature of 5°–10° C., then the cooling is ceased and the solution is stirred for another 30 minutes. The solution is poured into a mixture of 33 l of ice water and 16 l of 1.74M sodium hydrogensulphate and extracted three times with a 2:1 mixture of tetrahydrofuran and ethyl acetate. The organic phases are combined and extracted with saline, thereafter dried and evaporated. The 1,2-5,6-dianhydro-3,4-bis(β-carboxypropionyl)-dulcitol crystallizes upon cooling.

The weight of the filtered product is 2.73 kg. Yield: 79%. M.P.: 142°–144° C.

EXAMPLE 3

1,2-5,6-dianhydro-3,4-bis(β-carboxypropionyl)-dulcitol

The procedure of Example 2 is followed except that 148 g (1 mole) of 4-pyrrolidino pyridine are used instead of 4-dimethylamino pyridine. 2.59 kg of the title compound are obtained. Yield: 75%, M.P.: 142°–144° C.

We claim:

1. A process for preparing a compound of the Formula (I)

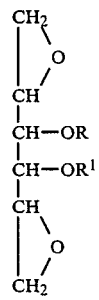

wherein R and R¹ are each $C_3$ to $C_6$ alkanoyl substituted by a free carboxy group and the configuration of the Formula (I) skeleton is that of dulcitol, mannitol, or iditol, which comprises the steps of:

(a) acylating a hexitol of the Formula (II)

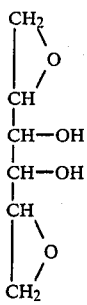

wherein the configuration of the Formula (II) skeleton is that of dulcitol, mannitol, or iditol, with a compound of the Formula (III)

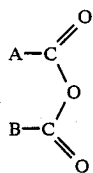

wherein A and B together form an alkylene group having 2 to 5 carbon atoms, at a temperature of 0° to 30° C. in the presence of a trialkylamine acid binding agent in a dipolar aprotic solvent selected from the group consisting of dimethyl sulfoxide and dimethyl formamide and in the presence of a catalyst selected from the group consisting of 4-dimethylaminopyridine and 4-pyrrolidino-pyridine, to form a solution containing as an intermediate a carboxylate salt of the monoacyl compound corresponding to the diacyl compound of the Formula (I) and formed with the trialkylamine acid binding agent;

(b) continuing the acylation reaction to completion to obtain the compound of the Formula (I) in solution in the form of its diacyl salt; and (c) acidifying the solution formed in step (b) with sodium hydrogen sulfate to yield the desired compound of the Formula (I).

2. The process defined in claim 1 which further comprises the step of recovering the compound of the Formula (I) by extracting the compound from the solution with an organic solvent.

3. The process defined in claim 1 wherein in step (a) the trialkylamine acid binding agent is triethylamine.

4. The process defined in claim 1 wherein in step (a) the dipolar aprotic solvent is dimethyl sulfoxide.

5. The process defined in claim 1 wherein in step (a) the catalyst is employed n a molar ratio of 0.01 to 1 per mole of the compound of the Formula (II).

* * * * *